US00PP30723P2

(12) United States Plant Patent
Van Swieten

(10) Patent No.: US PP30,723 P2
(45) Date of Patent: Jul. 16, 2019

(54) ***PHALAENOPSIS* ORCHID PLANT NAMED 'PHALKUZEL'**

(50) Latin Name: ***Phalaenopsis* hybrid**
Varietal Denomination: PHALKUZEL

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,272

(22) Filed: Oct. 25, 2018

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALKUZEL', particularly characterized by having copper flowers with small light purple centers and red dotted lips, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALKUZEL'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALKUZEL'.

The new *Phalaenopsis* plant is a product of a planned breeding program conducted by the inventor in Bleiswijk, The Netherlands. The objective of this breeding program was to create a new *Phalaenopsis* plant with numerous attractive copper flowers with small light purple centers and red dotted lips, suitable for potted plant production.

The new *Phalaenopsis* plant 'PHALKUZEL' is a result of cross-pollination made by the inventor in March 2008 in Bleiswijk, The Netherlands, of the proprietary female, or seed parent, *Phalaenopsis* hybrid '22286-02' (unpatented) with the proprietary male, or pollen parent, *Phalaenopsis* hybrid '22792-02' (unpatented).

The new *Phalaenopsis* was selected by the inventor as a single plant within the progeny of the stated cross-pollination in a controlled greenhouse in Bleiswijk, The Netherlands, in February 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have not been applied for to date. 'PHALKUZEL' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALKUZEL' as a new and distinct variety of *Phalaenopsis* plant.

1) Copper flowers with small light purple centers and red dotted lips;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in August 2018. Colors in the photographs may differ from the color values cited in the detailed botanical description, which accurately describe the actual colors of the new variety.

DESCRIPTION OF THE NEW VARIETY

Figure 1:
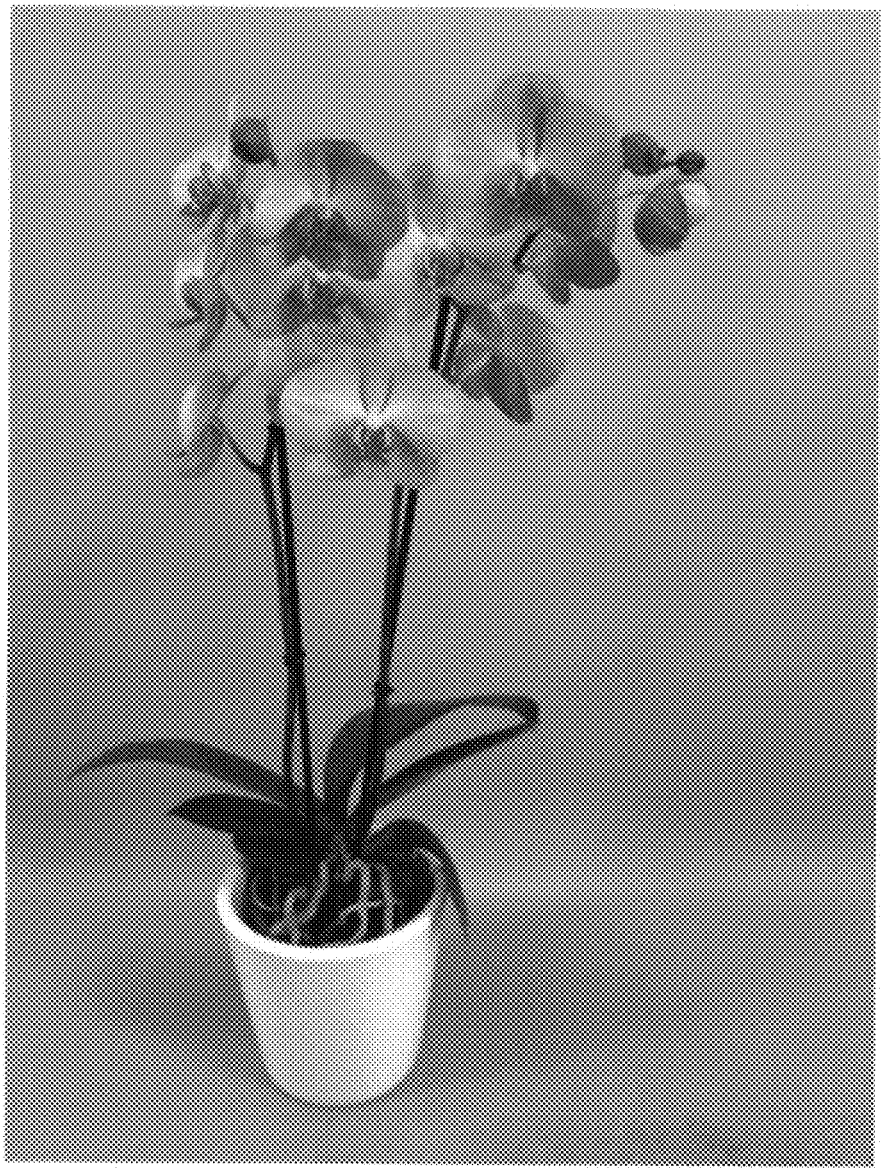
FIG. 1 shows the overall plant habit, including blooms, buds and foliage of 'PHALKUZEL'.
Figure 2:
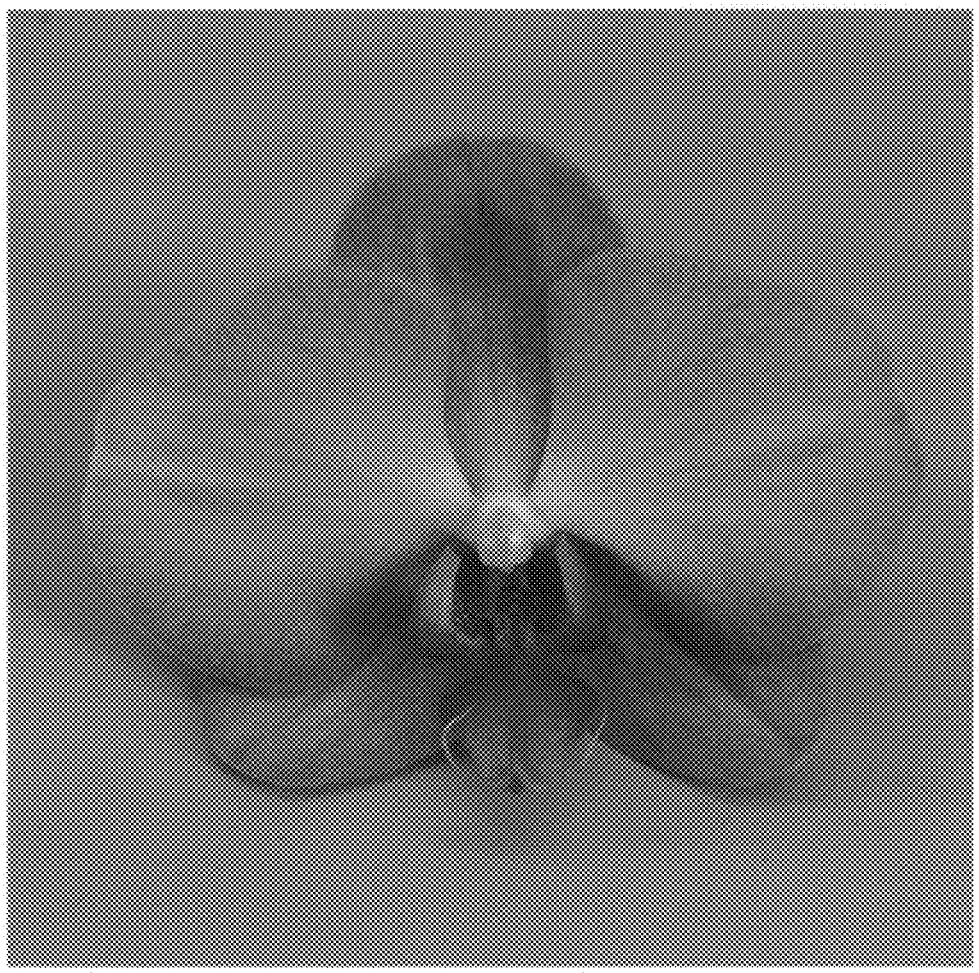
FIG. 2 shows a close-up of a flower of 'PHALKUZEL'.
Figure 3:
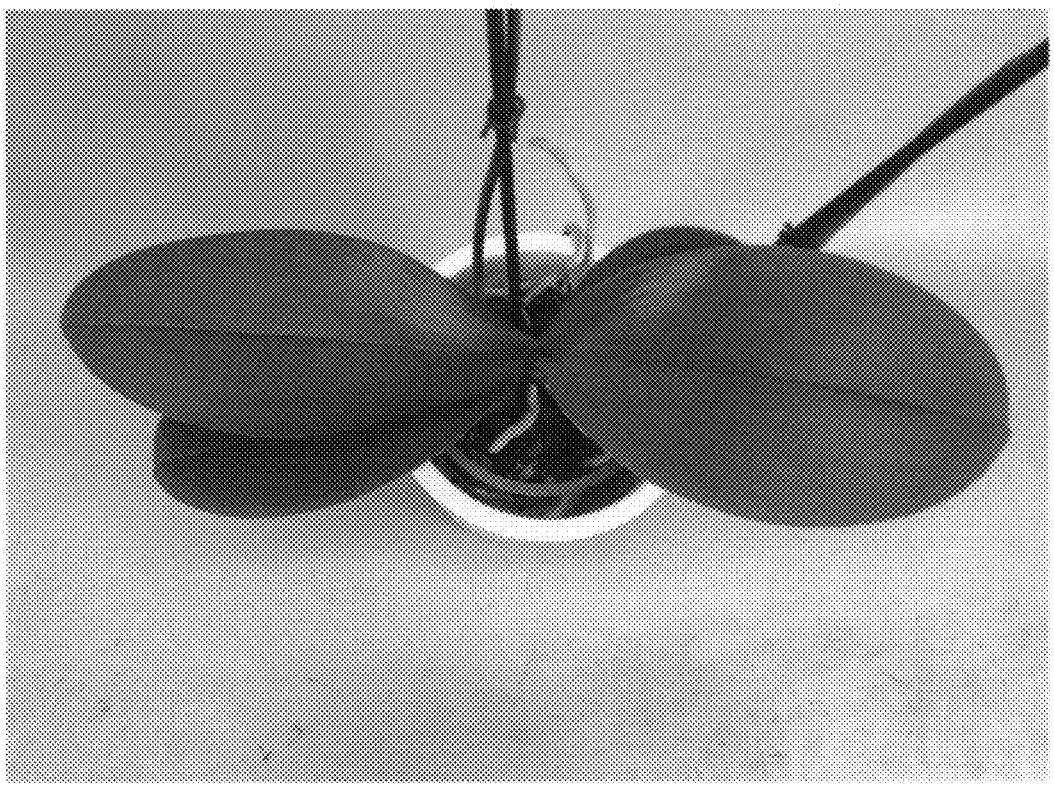
FIG. 3 shows an overhead view of the leaves of 'PHALKUZEL'.

The following detailed description sets forth the distinctive characteristics of 'PHALKUZEL'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in August 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALKUZEL'.

Parentage:

*Female parent*.—*Phalaenopsis* cultivar '22286-02' (unpatented).

*Male parent*.—*Phalaenopsis* cultivar '22792-02' (unpatented).

Propagation:

*Type*.—Meristem tissue culture.

Roots:

*Root description*.—Greyed-green colored roots (RHS 190B/C) with branching lateral roots having diluting purple (RHS N77A) and light green (RHS 146C) colored root tips.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with raceme inflorescence.

*Height* (*from soil level to top of inflorescence*).—Approximately 39.0 cm to 44.0 cm.

*Width* (*measured from leaf tips*).—About 30.0 cm to 32.0 cm.

*Vigor*.—Moderate.

Leaves:

*Mature leaves*.—Quantity per plant: 6 to 8 leaves are produced before flowering. Length (fully expanded): 17.0 cm to 19.0 cm. Width: 8.5 cm to 9.5 cm. Shape: Oblong. Base shape: Moderately elongated. Apex: Obtuse to rounded unequal. Leaf blade angle with the petiole (measured from the horizontal position): Between 20 degrees and 35 degrees. Leaf margin: Entire. Color: Upper surface: RHS 146B to 146C. Lower surface: RHS 146D. Texture (upper surface): Slightly rough. Thickness: 2.1 mm to 2.4 mm. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—4 to 10.

*Length*.—39.0 cm to 44.0 cm.

*Diameter*.—5.1 mm to 5.4 mm.

*Strength*.—Strong.

*Aspect*.—Upright to slightly pendant.

*Texture*.—Smooth.

*Color*.—Green (RHS 146B) with a touch of brown (RHS 200B).

*Internode length*.—6.0 cm to 7.0 cm.

*Callosities*.—None.

Inflorescence description:

*Appearance*.—Upright to slightly pendant, raceme inflorescence with bilaterally symmetrical flowers that open in succession beginning with the lowermost flower.

*Inflorescence size*.—Height (from base to tip): 120.0 mm to 150.0 mm.

*Flowering time*.—First flowers can be expected 10 to 11 months after planting in a 12 cm (diameter) pot.

*Flower*.—Height: 73.0 mm to 78.0 mm. Diameter: 83.0 mm to 88.0 mm. Depth of lip: 24.0 mm to 25 0 mm.

*Flower longevity*.—On the plant: 10 to 14 weeks.

*Fragrance*.—Absent.

*Flower bud*.—Average size: Large. Length: 20.0 mm to 22.0 mm. Width: 15.0 mm to 17.0 mm. Shape: Egg shaped. Color: Slightly green (RHS 146D) at the base; dark red (RHS 187B) toward the tip.

*Petals*.—Arrangement: Open/free. Shape: Semi-circular. Apex: Rounded asymmetric. Margin: Slightly undulated. Length (from base to tip): 39.0 mm to 41.0 mm. Width: 46.0 mm to 48.0 mm. Color (when fully opened): Upper surface: Basic color: Yellow (RHS 9C). Over color: Slightly light purple (RHS 76B) at the base and red shade (RHS 182B) toward the margin. Lower surface: Basic color: Light yellow (RHS 9D). Over color: Very light purple (RHS 76C) and dark pink shade (RHS 182C).

*Dorsal sepal*.—Shape: Elliptic. Apex: Rounded symmetric. Margin: Entire. Length (froth base to tip): 43.0 mm to 45.0 mm. Width: 34.0 mm to 36.0 mm. Color (when fully opened): Upper surface: Basic color: Yellow (RHS 9B). Over color: Very light purple (RHS 76B) at the base and red shade (RHS 182B) toward the margin. Lower surface: Basic color: Light yellow (RHS 160B). Over color: Dark pink shade (RHS 182C).

*Lateral sepals*.—Shape: Ovate. Apex: Obtuse asymmetric. Margin: Entire. Length (from base to tip): 38.0 mm to 40.0 mm. Width: 29.0 mm to 31.0 mm. Color (when fully opened): Upper surface: Basic color: Yellow (RHS 9C and 162C). Over color: Red spots (RHS 185A) at the base and red shade (RHS 182B) toward margin. Lower surface: Basic color: Yellow (RHS 160A). Over color: Dark pink shade (RHS 182C).

*Labellum* (*lip*).—Whiskers: Present. Length of whiskers: 8.0 mm to 10.0 mm. Color of whiskers: Light purple (RHS 76A) at the base, dotted (RHS 60A) with yellow tip (RHS 12A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated. Length: 15.0 mm to 17.0 mm. Width: 8.0 mm to 10.0 mm. Color: Slightly yellow (RHS 12A) at the base; white (RHS NN155C) striped (RHS 183B); red (RHS 185A) toward one margin and red-purple (RHS N78B) toward tip.

*Apical lobe*.—Shape: Rhombic. Margin: Entire. Length: 18.0 mm to 20.0 mm. Width: 17.0 mm to 19.0 mm. Color: Yellow (RHS 13A) at the base and along the midvein; red (RHS 185A) toward wings; dotted (RHS 184C).

*Callus*.—Average size: Small. Height: 4.0 mm to 5.0 mm. Length: 4.0 mm to 5.0 mm. Width: 3.0 mm to 4.0 mm. Color: Yellow (RHS 13A) dotted (RHS 183B).

Reproductive organs:

*Column*.—Length: 8.0 mm to 10.0 mm. Diameter: 5.0 mm to 5.3 mm. Color: Light purple (RHS 76A).

*Pollinia*.—Quantity: 2. Diameter: 0.9 mm to 1.1 mm. Color: Yellow-orange (RHS 23A).

*Ovary*.—Length: 7.0 mm to 9.0 mm. Diameter: 2.2 mm to 2.4 mm. Color: Light green (RHS 145C) and very light purple (RHS 76C) towards the flower.

*Pedicel*.—Length: 34.0 mm to 36.0 mm. Diameter: 2.5 mm to 2.7 mm. Color: Green (RHS 146C) at the base; light green (RHS 145C) and very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALKUZEL' differs from female parent plant '22286-02' (unpatented) in that 'PHALKUZEL' has a main flower color of yellow and a main apical lobe color of red, whereas '22286-02' has a main flower color of greenish-yellow and a main apical lobe color of yellow. Additionally, 'PHALKUZEL' has larger flowers than '22286-02'.

'PHALKUZEL' differs from male parent plant '22792-02' (unpatented) in that 'PHALKUZEL' has a main flower color of yellow, whereas '22792-02' has a main flower color of reddish-purple. Additionally, 'PHALKUZEL' has smaller flowers than '22792-02'.

'PHALKUZEL' is most similar to the commercial *Phalaenopsis* plants named 'PHALDIQYK' (U.S. Plant Pat. No. 27,342) and 'PHALIFQUDI' (U.S. Plant Pat. No. 26,831). 'PHALKUZEL' differs from the commercial variety 'PHALDIQYK' in that 'PHALKUZEL' has obtuse to rounded unequal leaf apexes, whereas 'PHALDIQYK' has unequal mucronate leaf apexes. Additionally, 'PHALKUZEL' has smaller flowers and wider leaves than 'PHALDIQYK'.

'PHALKUZEL' differs from the commercial variety 'PHALIFQUDI' in that 'PHALKUZEL' has weakly spatulate lateral lobes and obtuse to rounded unequal leaf apexes, whereas 'PHALIFQUDI' has spatulate lateral lobes and unequal mucronate leaf apexes. Additionally, 'PHALKUZEL' has larger flowers and wider dorsal sepals than 'PHALIFQUDI'.

I claim:

1. A new and distinct variety of *Phalaenopsis* plant named 'PHALKUZEL', substantially as described and illustrated herein.

* * * * *